(12) United States Patent
Ban et al.

(10) Patent No.: US 8,815,299 B2
(45) Date of Patent: Aug. 26, 2014

(54) METHOD FOR OBTAINING A NATURAL MIXTURE OF CONJUGATED EQUINE ESTROGENS DEPLETED IN NON-CONJUGATED LIPOPHILIC COMPOUNDS

(75) Inventors: Ivan Ban, Hannover (DE); Klaus-Guenter Gerling, Winsen/Aller (DE); Hans-Joerg Mueller, Hannover (DE); Stefan Wachsmann, Hannover (DE)

(73) Assignee: Abbott Products GmbH, Hannover (DE)

( * ) Notice: Subject to any disclaimer, the term of this patent is extended or adjusted under 35 U.S.C. 154(b) by 951 days.

(21) Appl. No.: 12/138,808

(22) Filed: Jun. 13, 2008

(65) Prior Publication Data

US 2009/0023699 A1    Jan. 22, 2009

Related U.S. Application Data

(63) Continuation of application No. 10/681,284, filed on Oct. 9, 2003, now abandoned.

(60) Provisional application No. 60/448,532, filed on Feb. 21, 2003.

(30) Foreign Application Priority Data

Oct. 11, 2002    (EP) .................................. 02022763

(51) Int. Cl.
*A61K 35/22* (2006.01)
*A61K 31/56* (2006.01)

(52) U.S. Cl.
USPC ........................... 424/546; 424/545; 514/182

(58) Field of Classification Search
USPC ................... 424/545, 546; 518/182
See application file for complete search history.

(56) References Cited

U.S. PATENT DOCUMENTS

| 2,429,398 A | 10/1947 | Cook et al. |
| 2,519,516 A | 8/1950 | Turner et al. |
| 2,551,205 A | 5/1951 | Cook et al. |
| 2,565,115 A | 8/1951 | Bates et al. |
| 2,696,265 A | 12/1954 | Beall et al. |
| 2,834,712 A | 5/1958 | Beall et al. |
| 5,071,565 A | 12/1991 | Fritz et al. |
| 5,723,454 A | 3/1998 | Ban et al. |
| 5,814,624 A * | 9/1998 | Ban et al. ...................... 514/170 |

FOREIGN PATENT DOCUMENTS

| CN | 1308083 A | 8/2001 |
| EP | 0 770 388 A1 | 6/1997 |
| EP | 1 064 008 A1 | 11/2000 |
| EP | 1 166 643 A1 | 1/2002 |
| JP | 7-509606 A | 10/1995 |
| JP | 2000-517309 | 12/2000 |
| RU | 2 113 849 C1 | 6/1998 |
| RU | 2 160 740 C2 | 12/2000 |
| RU | 2 179 029 C2 | 2/2002 |
| WO | WO 94/03606 A1 | 2/1994 |
| WO | WO 96/10031 A1 | 4/1996 |
| WO | WO 98/08525 A1 | 3/1998 |
| WO | WO 98/08526 A1 | 3/1998 |
| WO | WO 98/49153 A1 | 11/1998 |
| WO | WO 00/32204 A1 | 6/2000 |
| WO | WO 01/27134 A1 | 4/2001 |
| WO | WO 01/53285 A1 | 7/2001 |
| WO | WO 02/074292 A2 | 9/2002 |

OTHER PUBLICATIONS

Cohen et al. "The Preparation of Pregnancy Urine for an Estrogen Profile" Steroids 32:2; 1978, pp. 279-293.*
Cornell Material Safety Data Sheets—"Phenol"—Jan. 1, 1997, 8 pgs.
ICSC—International Chemical and Safety Cards—"m-Cresol and p-Cresol" 1993, 3 pgs.
Hurst: Methods of Analysis of Foods and Nutraceuticals, p. 228; CRC Press; Apr. 2002, 3 pgs.
Klaassen et al: Casarett and Doull's Toxicology: The basic science of poisons; p. 264; McGraw Hill, 3 pgs.
Nendza: Structure-activity relationships in environmental science; Chapman & Hall, 1998, 7 pgs.
Fishman et al: Two dimensional thin layer chromatography of extradiol and estroil glucosiduronic acids, Steroids Mar. 1965 10 pgs.
The Merch Index: Def. Of Androstane (p. 107 and Pregnane (p. 1326), Merck and Co. Inc. 1996, 5 pgs.
Neeb, P.; Horie, O.; Moortgat, G.K. et al: The ethene-ozone reaction in the gas phase; In: J. Phys., J. Phys Chem. A 1998, 102, pp. 6778-6785.
Grotewold, E.: The Science of Flavonoids; Springer-Science 2006, p. 51.
Inderjit, K.M.M.; Dakashini, C.L.F.: Principles and practices in plant ecology; CRC press 1999, p. 275.
The Dielectric Constant and Solubility; www.utmem.edu/physpharm/.021e3.html, accessed Dec. 13, 2007 1page.
Wikipedia "Solvent"; http://en.wikipedia.org/wiki/Solvent, accessed Dec. 13, 2007, 9 pgs.
Marrian et al., Equol, a new inactive phenol Isolated from the ketohydroxyoestrin fraction of mares: In:, Biochem J. 1932; 26(4) : 1227-1232.
Cohen et al., "The preparation of pregnancy urine for an estrogen profile", In: Steroids; vol. 32 (2), pp. 279-293, 1978.

* cited by examiner

*Primary Examiner* — Thane Underdahl
(74) *Attorney, Agent, or Firm* — Crowell & Moring LLP

(57) ABSTRACT

A method for obtaining an extract containing the natural mixture of conjugated equine estrogens by liquid-liquid extraction of the mixture of conjugated equine estrogens, wherein the mixture obtained is depleted in non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds.

15 Claims, No Drawings

METHOD FOR OBTAINING A NATURAL MIXTURE OF CONJUGATED EQUINE ESTROGENS DEPLETED IN NON-CONJUGATED LIPOPHILIC COMPOUNDS

CROSS REFERENCE TO RELATED APPLICATIONS

The present application is a continuation application of application Ser. No. 10/681,284, filed Oct. 9, 2003, now abandoned which claims priority under 35 U.S.C. §119 based on European Patent Application No. 02 02 2763.3, filed Oct. 11, 2002, and based on U.S. Provisional Patent Application No. 60/448,532, filed Feb. 21, 2003, the disclosures of which are incorporated herein by reference in their entireties.

BACKGROUND OF THE INVENTION

The present invention relates to obtaining a natural mixture of conjugated equine estrogens which is depleted in non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds.

Estrogens are used in medicine for hormone replacement therapy. In particular, estrogen mixtures are used for the treatment and prophylaxis of disorders of the climacteric period which occur in women after natural or artificial menopause. In this case, natural mixtures of conjugated estrogens such as are found in the urine of pregnant mares, hereafter referred to as natural mixtures of conjugated equine estrogens, have proved particularly effective and readily compatible.

The dissolved solids content in the urine of pregnant mares (=pregnant mares' urine, abbreviated hereafter as "PMU") can naturally fluctuate within wide ranges, and may generally lie in a range of 40 to 90 g dry matter per liter. In addition to urea and other usual urine contents, the solids content of the PMU contains phenolic constituents in quantities of about 2 to 5% by weight relative to the dry matter. These phenolic constituents include cresols and dihydro-3,4-bis[(3-hydroxyphenyl)methyl]-2(3H)-furanone, known as HPMF. These may be present in free or conjugated form.

The PMU contains a natural mixture of estrogens which is largely present in conjugated form, e.g. as sulfuric acid semiester sodium salt (abbreviated hereafter as "sulfate salt"). The conjugated estrogen content (calculated as estrogen sulfate salt) may be between 0.1 and 1% by weight, relative to the dry matter. In addition, further lipophilic compounds may be present in the solids content of the PMU, the quantities of which compounds can fluctuate within wide ranges and cannot be predicted. These lipophilic compounds originate predominantly from the plants ingested as food by the pregnant mares and primarily comprise various flavonoid, isoflavonoid and norisoprenoid derivatives and comparable compounds, such as for example formononetin, genistein, daidzein, biochanin A, equol and coumestrol. These lipophilic compounds originally of plant origin may be present in the urine in conjugated or in free (non-conjugated) form. The lipophilic constituents furthermore occurring in the solids content of the PMU also include non-conjugated steroid derivatives; notably including in particular the androstane and pregnane steroids and also non-conjugated estrogen derivatives.

Extracts containing natural mixtures of conjugated estrogens are usually obtained either by a solid-phase extraction method or by a method based on various liquid-liquid extraction steps with organic solvents which are not miscible, or only slightly miscible, with water. Generally speaking, in order to be able to be used as active substance constituent for pharmaceuticals, the natural mixture of conjugated estrogens which is obtained must meet certain pharmaceutical specifications, for example, the specification laid down in the USP (United States Pharmacopeia) or European Pharmacopoeia. For example, certain limit values must be observed with regard to the content of conjugated estrogens relative to the dry matter.

U.S. Pat. No. 2,551,205 and U.S. Pat. No. 2,429,398 describe a process for the preparation of a water-soluble estrogen preparation from PMU, in which initially an aqueous concentrate is obtained by adsorption on activated carbon or other suitable adsorber materials, elution with a water-miscible organic solvent, such as pyridine, and subsequent removal of the solvent, thereby yielding a concentrate which contains the major part of the water-soluble estrogen constituents of the original PMU. Whereas in U.S. Pat. No. 2,429,398 the concentrate is further purified by extraction with benzene and/or ether, U.S. Pat. No. 2,551,205 discloses acidulating the concentrate to a pH value of between 2 and 6, preferably between 4 and 5, and then rapidly extracting it with an organic solvent which is only slightly miscible with water selected from aliphatic, aromatic or alicyclic hydrocarbons (e.g. hexane, benzene, toluene, cyclohexane) or the chlorinated hydrocarbons (e.g. chloroform, ethylene dichloride, trichloroethylene, carbon tetrachloride, chlorobenzene), in order to separate undesirable substances such as fats, oils, free phenolic constituents and the non-conjugated steroids by transfer into the organic phase. Finally, the aqueous phase is stabilized by neutralization. U.S. Pat. No. 2,551,205 recommends further purifying the resulting extract by subsequent extraction steps and precipitation operations. Overall, after performing the method described in U.S. Pat. No. 2,551,205, a yield of only about 80% of the estrogen constituents of the concentrate used is obtained.

U.S. Pat. No. 2,565,115 describes the extraction of the conjugated estrogens from PMU with acetone. No statement is made about the purity of the resulting estrogen fraction.

U.S. Pat. No. 2,696,265 describes a method in which initially the estrogens are extracted with an aliphatic alcohol or ketone, such as hexanol, cyclohexanol or cyclohexanone. The estrogens pass into the organic phase and are then further purified; inter alia, an aqueous phase containing the estrogens is adjusted to a pH value of 4 with hydrochloric acid and extracted with ethylene dichloride.

U.S. Pat. No. 2,834,712 discloses a method for the preparation of estrogen mixtures of significant purity and low toxicity which is based on a large number of individual extraction steps with different solvents and the setting of different pH values. In that method, large volumes of solvents such as hexane and benzene are used. Thus, for example, in one step an already purified concentrate is dissolved in water, adjusted with hydrochloric acid to a pH value of approximately 5.0 and extracted with benzene and then with ether, in order to separate the phenolic constituents.

International patent application WO 01/27134 describes a comparatively simple method of extracting conjugated estrogens from PMU: after the addition of a salt, such as sodium chloride, the PMU is extracted with at least the same volume percent of an organic solvent, such as ethyl acetate, whereupon the conjugated estrogens pass into the organic phase. The organic phase is separated and dried in order to obtain the extract. No statements are made in WO 01/27134 about the purity of the conjugated estrogen extract which is obtained.

With the liquid-liquid-extraction method described above and known from the prior art, however, a number of problems occur, such as vigorous foaming, sediment formation, emulsification and poor phase separation. Generally several extraction steps are required, which results in losses and only partial recovery of the estrogen content. Furthermore, these extraction methods require large volumes of solvents some of which are harmful to health. Furthermore, in the patent specifications listed above no statements are made either about the content of non-conjugated lipophilic constituents, such as for example non-conjugated flavonoid, isoflavonoid and norisoprenoid derivatives and comparable non-conjugated compounds, or also non-conjugated steroids, in particular androstane and pregnane steroids, in the products obtained, nor about separation of these constituents. These methods known from the prior art either provide no satisfactory results with regard to the yield or with regard to the purity of the extract obtained, measured by the total hormone content obtained relative to the dry matter, or they are based on a large number of different method steps and the use of large volumes of organic solvents some of which are undesirable from an environmental or toxicological point of view.

Furthermore various solid-phase-extraction methods are known from the prior art for obtaining a natural mixture of conjugated equine estrogens largely depleted in phenolic urine contents. Thus international patent application WO 98/08526 describes a method with which a largely cresol- and HPMF-free mixture, which is depleted in phenolic urine content and contains practically the entire natural estrogen content of the PMU, can be obtained in a solid-phase extraction on a semipolar, in particular non-ionic semipolar, polymeric adsorption resin. International patent application WO 98/08526 describes a similar method in which silica gel is used as the adsorber material in the solid-phase extraction. Also Chinese patent application CN 1308083 describes a comparable method in which polar adsorption resins containing cyano groups are used. The extracts obtained are suitable as starting material for the preparation of pharmaceuticals which contain the natural mixture of conjugated estrogens from PMU as active substance constituent.

The established pharmaceutical specifications, for example, the limits to be observed regarding the content of conjugated estrogens relative to dry matter, are normally met by the mixtures of conjugated estrogens obtained from PMU in accordance with the method of WO 98/08526 or the method of WO 98/08525. It has, however, turned out that in addition to the desired content of conjugated estrogens also non-conjugated lipophilic compounds may be contained in the dry matter obtained. The non-conjugated lipophilic compounds include, for example, various non-conjugated flavonoid, isoflavonoid and norisoprenoid derivatives and comparable non-conjugated compounds, such as, for example, formononetin, genistein, daidzein, biochanin A, equol and coumestrol, but also non-conjugated steroids, in particular androstane and pregnane steroids, and non-conjugated estrogens. This list should not be regarded as exhaustive, however, since other non-conjugated compounds also may be present. The presence of the non-conjugated lipophilic compounds in the mixture of conjugated estrogens obtained from the PMU cannot be standardized, but both the content and the composition of the free and conjugated lipophilic compounds varies, for example, depending on the food ingested by the pregnant mares.

Although the composition of the natural mixture of conjugated equine estrogens does not change due to the additional presence of the non-conjugated lipophilic compounds, the content of the conjugated equine estrogens relative to the dry matter can be reduced. A higher concentration of the active substances, i.e. the conjugated equine estrogens, in the extract obtained could be achieved by deliberate separation of the non-conjugated lipophilic constituents. Also for reasons of medicament safety it may be useful to remove the non-conjugated lipophilic compounds in order to ensure a uniform composition of individual extract batches, since in this way the non-conjugated lipophilic constituents, the content and composition of which in the PMU can vary according to the seasonally changing type of food ingested by the pregnant mares, can be eliminated, and thus the resulting extracts would all have a comparable content of conjugated equine estrogens relative to the dry matter. Furthermore, separation of the non-conjugated lipophilic compounds may be advantageous in order to obtain a uniform physiological spectrum of action. For example, it may be useful to separate possibly present, non-conjugated lipophilic compounds, which may possibly themselves have an undesirable physiological effect, from the natural mixture of conjugated equine estrogens.

SUMMARY OF THE INVENTION

It is therefore an object of the present invention to provide a technically and economically optimum method for obtaining a natural mixture of conjugated equine estrogens, from which non-conjugated lipophilic compounds, in particular of non-conjugated flavonoid, isoflavonoid and norisoprenoid derivatives, are largely depleted.

Another object of the invention is to provide a method for obtaining a natural mixture of conjugated equine estrogens in which only small quantities of solvent which is not harmful to the health are used.

A further object is to provide a method for obtaining a natural mixture of conjugated equine estrogens which comprises only a few method steps and yields a conjugated equine estrogen extract with a comparatively high content of conjugated estrogens relative to the dry matter.

An additional object is to provide a method for obtaining a natural mixture of conjugated equine estrogens which makes it possible in a simple manner to treat a mixture of conjugated estrogens from pregnant mares' urine already depleted in phenolic urine contents, which may contain changing and possibly elevated quantities of non-conjugated lipophilic compounds such that the natural mixture of conjugated equine estrogens obtained has good active substance contents and meets the required pharmaceutical specifications.

A particular object is to provide a method for obtaining a natural mixture of conjugated equine estrogens which satisfies the required limits on the content of conjugated estrogens relative to dry matter.

A method has now been found which, in a surprisingly simple manner, produces a mixture of conjugated equine estrogens from a changing PMU having possibly elevated quantities of non-conjugated lipophilic compounds, the mixture of conjugated equine estrogens obtained being largely depleted in non-conjugated lipophilic compounds, in particular non-conjugated flavonoid, isoflavonoid and norisoprenoid derivatives. In particular, the method according to the invention can be applied to a mixture of conjugated estrogens from pregnant mares' urine already depleted in phenolic urine contents, so that with the method a mixture of conjugated equine estrogens is obtained which has a high product quality and reliably satisfies the applicable pharmaceutical specifications, in particular also pertaining to the limits to be observed with regard to the content of conjugated estrogens relative to the dry matter.

The method according to the invention for obtaining a natural mixture of conjugated equine estrogens is characterized in that the resulting mixture is depleted in non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds, and comprises the steps of:

a) subjecting an aqueous initial phase selected from the group consisting of:
  (i) an aqueous solution of a natural mixture of conjugated estrogens from pregnant mares' urine already depleted in phenolic urine contents,
  (ii) an aqueous concentrate of a natural mixture of conjugated estrogens from pregnant mares' urine already depleted in phenolic urine contents,
  (iii) a concentrate of a urine liquid, and
  (iv) a urine concentrate, optionally pre-purified by filtration, to a liquid-liquid extraction with a sufficient quantity of an extracting agent which represents an organic solvent suitable for the extraction of non-conjugated lipophilic compounds from the above group, and which is not miscible, or only slightly miscible, with water, and subsequently separating the resulting aqueous phase, and b) optionally repeating method step (a) with the resulting aqueous phase, and c) recovering an aqueous phase containing the natural mixture of conjugated estrogens, and optionally concentrating the recovered aqueous phase.

For the method according to the invention (i) an aqueous solution of a natural mixture of conjugated estrogens from pregnant mares' urine already depleted in phenolic urine contents, or (ii) an aqueous concentrate of a natural mixture of conjugated estrogens from pregnant mares' urine already depleted in phenolic urine contents may be used as aqueous initial phase. This aqueous solution or this aqueous concentrate may be obtained by a method such as has already been described for example in international patent applications WO 98/08526 and WO 98/08525 or in Chinese patent application CN 1308083 and is thus familiar to persons skilled in the art from these published patent applications. The contents of WO 98/08526, WO 98/08525 and CN 1308083 are also hereby incorporated by reference into the disclosure of the present application. An aqueous solution or an aqueous concentrate of a natural mixture, already depleted in phenolic urine contents, of conjugated estrogens from pregnant mares' urine may also be the product of a liquid-liquid extraction process, such as described, for example, in international patent application WO 01/27134. The aqueous solutions or concentrates obtained according to the methods described in the above patent applications can be further concentrated in known manner, such as for example by distillation, in order to obtain a concentrate largely freed of organic solvent before their use in the method according to the invention.

Furthermore (iii) a concentrate obtained from the PMU by concentration or (iv) a concentrate obtained from the PMU, which has already been pre-purified by filtration or comparable methods may be used as aqueous initial phase for the method according to the invention. The collected urine (PMU) is first freed in known manner from mucilaginous substances and solids. Advantageously, solids and mucilaginous substances are allowed to settle and are then separated using known separation methods, for example decanting, separation and/or filtering. Thus the PMU may be passed, for example, through a known separating means, e.g. a separator, a filtration unit or a sedimenter. A sand bed, for example, may serve as separating means, or commercially available separators may be used, e.g. nozzle or chamber separators. If desired, a microfiltration unit or an ultrafiltration unit may also be used, and if these are used, it is possible to simultaneously achieve a largely bacteria-free and virus-free filtered PMU. If desired, preservatives, germicides, bactericides and/or anthelmintics may be added to the urine or the urine concentrate.

A concentrated PMU retentate which can be obtained from the PMU by known membrane filtration can also be used as pre-purified urine concentrate (iv). The solids content of the retentate and the composition thereof may vary depending on the PMU used and the membrane used for the membrane filtration, for example the pore width thereof, and also the conditions of filtration. For example, when using a nanofiltration membrane virtually loss-free concentration of the estrogen content in the PMU retentate can be achieved while simultaneously removing up to 50% by weight of the low-molecular PMU contents. PMU retentates which have been concentrated up to a ratio of approximately 1:10, for example a ratio of approximately 1:7, and the volume of which can thus be concentrated to approximately 1/10, for example approximately 1/7, of the original PMU volume can be used for the method according to the invention.

If the concentrate used as aqueous initial phase is a reduced concentrate of the PMU or a PMU concentrate for example already pre-purified by membrane filtration, then the mixture of conjugated equine estrogens obtained, which has been depleted in non-conjugated lipophilic compounds by the method according to the invention, may already have sufficient purity, but may possibly still contain significant quantities of phenolic urine contents, which have to be removed by further method steps. Thus with the aqueous phase obtained, for example, a method can be carried out such as has been described in international patent applications WO 98/08526 and WO 98/08525 or in Chinese patent application CN 1308083 and is thus familiar to persons skilled in the art from these published patent applications, in order to obtain a product which also meets the necessary pharmaceutical specifications for conjugated estrogens with regard to the content of phenolic urine constituents.

Within the context of this invention, the use of an aqueous solution of a natural mixture of conjugated estrogens from pregnant mares' urine already depleted in phenolic urine contents, or an aqueous concentrate of a natural mixture of conjugated estrogens from pregnant mares' urine already depleted in phenolic urine contents as the aqueous initial phase is regarded as being particularly preferable.

According to the invention, in method step (a) with the aqueous initial phase described further above a liquid-liquid extraction is carried out with a sufficient quantity of an extracting agent which represents an organic solvent which is not miscible, or only slightly miscible, with water and is suitable for the extraction of non-conjugated lipophilic compounds, in particular of non-conjugated flavonoids, non-conjugated isoflavonoids, non-conjugated norisoprenoids and non-conjugated steroids. Furthermore, the organic solvent should not be miscible, or only slightly miscible, with the aqueous initial phase. As used herein, the term "only slightly miscible" means that at most 6% by volume dissolved organic solvent is present in the aqueous phase. In principle, any organic solvent which is not miscible with water can be used for this liquid-liquid extraction step, as long as it extracts the non-conjugated lipophilic compounds from the aqueous phase. Suitable examples for the extraction of non-conjugated lipophilic compounds, in particular of non-conjugated flavonoids, non-conjugated isoflavonoids, non-conjugated norisoprenoids and non-conjugated steroids, include the following organic solvents with 1 to 10 carbon atoms, which may be arranged in a straight-chain, branched or cyclic configuration: $C_4$-$C_{10}$ alcohols (such as for example butanol, hexanol, cyclohexanol and pentanol), $C_2$-$C_{10}$ esterified acids (such as for example ethyl acetate, methyl acetate, propyl acetate, isopropyl acetate, butyl acetate, amyl acetate, ethyl methyl malonate, dimethyl phosphonate), $C_3$-$C_{10}$ aldehydes and $C_4$-$C_{10}$ ketones (such as for example butanone, pentanone, hexane-2,4-dione, hexanedial, cyclohexanecarbaldehyde, methyl phenyl ketone and the like), or generally $C_3$-$C_{10}$ alkoxy compounds, $C_2$-$C_{10}$ ethers (diethyl ether, methyl tert.-butyl ether), $C_3$-$C_6$ nitrites, and $C_1$-$C_3$ haloalkanes (methylene chloride), and also mixtures of the aforementioned solvents. $C_1$-$C_4$-alkyl acetates, hexanol, diethyl ether, methylene chloride, methyl tert.-butyl ether and mixtures of the aforementioned solvents are particularly useful as extracting agents in the present invention. Of this selection, $C_1$-$C_4$-alkyl acetates, and in particular ethyl acetate, represent the most preferred extracting agent.

In the liquid-liquid extraction with a sufficient quantity of an extracting agent performed according to the invention in method step (a), the volume ratio of the aqueous initial phase to the extracting agent should be understood to be non-limiting in the context of this invention. Generally, a volume of organic solvent is used which corresponds to the volume of the aqueous initial phase, but the ratio of aqueous to organic phase may lie within a range between 10:1 and 1:10. Preferably, the volume ratio of the aqueous initial phase to the organic extracting agent lies in the range from 5:1 to 1:3. A volume ratio in the range from 2:1 to 1:2 is particularly advantageous.

Persons skilled in the art will know how to perform such an extraction method from the prior art. Usually a liquid-liquid extraction is performed in an apparatus which permits continuous thorough mixing of the aqueous phase and the organic phase which is not miscible with water. For example, a device known as a mixer-settler apparatus, in which the two phases are mixed by stirring, is suitable for performing such an extraction process.

In principle, the liquid-liquid extraction described according to the invention can be carried out at any pH value of the aqueous initial phase. In a particularly preferred variant of the liquid-liquid extraction described according to the invention, in method step (a) initially the pH value of the aqueous initial phase is adjusted to a value in the range between 4 and 12. Preferably, the pH value is adjusted to a value in the range from 4.0 to 7.0, i.e. in the weakly acidic to neutral range. Particularly preferably, the pH value is adjusted to a value in the range from 4.0 to 6.0, very particularly in the range from 4.7 to 5.3.

During the adjustment of the pH value, the solution initially introduced is advantageously mixed thoroughly in a sufficiently large, inert container, such as for example a high-grade steel vat, with a stirrer or a comparable device, in order thus to assure rapid and uniform adjustment of the pH value. Conventional bases or acids may be used to adjust the pH. Thus, for example, one of the conventional inorganic or organic acids, advantageously a dilute acid, can be used to lower the pH value. For example, the use of dilute sulfuric acid, preferably 1 N sulfuric acid, dilute acetic acid, dilute phosphoric acid or dilute hydrochloric acid, preferably 1 N hydrochloric acid, has proved particularly suitable for lowering or setting a pH value less than 7.

The liquid-liquid extraction described according to the invention does not require a specific temperature to be set, but can be performed within a wide temperature range, which may be between 5° C. and the boiling point of the organic solvent or at most 95° C. Preferably, the liquid-liquid-extraction according to the invention is performed at room temperature, since the additional energy demand is then lowest. Usually ambient temperature is regarded as room temperature; for example, a temperature of between 10° and 30° C. is thus designated.

The duration of such a liquid-liquid extraction is regarded as not being limiting in the context of this invention, and may be between 5 minutes and several hours. The duration will fluctuate according to the quantity of aqueous initial phase used. Typically, the aqueous phase from method step (a) and the organic extracting agent are mixed together for 5 to 60 minutes, preferably for 10 to 20 minutes, in order to achieve as complete as possible transfer of the non-conjugated lipophilic constituents from the aqueous phase into the organic phase.

Following the step of extraction by thorough mixing, the phase mixture is allowed to stand in order to achieve separation of the phases. The phase separation may take a time of 10 minutes up to several hours, depending on the volumes used. Preferably the phases are allowed to stand for 30 to 120 minutes. When the aqueous phase and the organic phase have separated from each other, the aqueous phase is collected and kept for further use, while the organic phase is discarded.

The method step (a) described above may optionally be repeated. Thus step (a) is followed according to the invention by an optional method step (b), in which with the aqueous phase obtained from method step (a) is subjected again to a liquid-liquid extraction with a sufficient quantity of an extracting agent, which represents an organic solvent suitable for the extraction of non-conjugated lipophilic compounds, in particular of non-conjugated flavonoids, non-conjugated isoflavonoids, non-conjugated norisoprenoids and non-conjugated steroids, and which is not miscible, or only slightly miscible, with water.

The possibilities listed above under method step (a) should be regarded only as illustrative examples for the selection of the extracting agent and the manner of performing the extraction, i.e. the apparatus used, the duration and the temperature of the extraction process. According to the invention, either different extracting agents or the same extracting agent can be used in both method steps (a) and (b). Preferably the same extracting agent is used in both extraction steps. In particular, in both extraction steps $C_1$-$C_4$-alkyl acetates, but in particular ethyl acetate, should be used as extracting agent.

In the liquid-liquid extraction with a sufficient quantity of an extracting agent performed according to the invention in method step (b), the volume ratio of the aqueous phase from method step (a) which has already been extracted once and contains the conjugated equine estrogens to the extracting agent should be understood as non-limiting in the context of this invention. Generally, a volume of organic solvent is used which is clearly below the volume of the aqueous phase obtained from method step (a), but the ratio of aqueous to organic phase may lie within a range between 40:1 and 1:2. Preferably, the volume ratio of the aqueous phase obtained from method step (b) to the organic extracting agent lies in the range from 20:1 to 1:1. A volume ratio in the range from 10:1 to 2:1 is regarded as particularly advantageous.

Following the step of extraction by thorough mixing in method step (b), the phase mixture is allowed to stand in order to achieve separation of the phases. The phase separation may take a time of 10 minutes up to several hours, but preferably the phases are left to stand for 20 to 90 minutes. When the aqueous phase and the organic phase have separated from each other, the aqueous phase is collected and kept for further use, while the organic phase is discarded.

After the separation of the organic phase from the aqueous phase, in method step (c) an aqueous phase containing the natural mixture of conjugated estrogens is obtained. This aqueous phase contains the natural mixture of conjugated estrogens occurring in the PMU in addition to only an extremely small proportion of the content of non-conjugated lipophilic constituents originally present in the PMU or the prepared PMU concentrate(s). If desired, this aqueous phase can be concentrated further in known manner, in order to obtain a concentrate largely freed of organic solvent which is suitable for further processing. Thus, for example, the remaining residues of organic solvent can be distilled off from the resulting aqueous phase. The distillation means that the dry matter content of the aqueous extract phase can also be set to a concrete value, preferably to a dry matter content in the range between 5 and 15%, in particular to a dry matter content of 9%. Following this, to stabilize the natural mixture of conjugated equine estrogens obtained, the pH value of the aqueous extract solution can be adjusted to a value in the alkaline range, preferably in the range between 8 and 13, particularly preferably to a value between 9 and 12. Bases typically used for adjusting the pH value, for example 1N NaOH or $Na_2CO_3$, are suitable for adjusting the pH value in the invention.

The aqueous phase obtained according to the invention in method step (c), which has optionally been still further worked up or concentrated, can serve as the starting material for the preparation of medicaments containing the natural mixture of conjugated equine estrogens. If desired, an eluent-free solids mixture can also be produced by a suitable drying process, such as spray-drying. If the natural mixture of conjugated estrogens is to be used for the production of solid medicaments, it may be advantageous to admix a solid excipient with the aqueous phase containing the conjugated estrogens before concentration or drying in order to obtain a solids mixture containing the conjugated estrogens and excipients. Both the aqueous phase containing the estrogen mixture and a concentrate or dried solids product prepared therefrom can be processed in a known manner into solid or liquid galenic preparations such as, for example, tablets, coated tablets, capsules or emulsions. These galenic formulations can be prepared by known methods using conventional solid or liquid excipients, e.g. starch, cellulose, lactose or talcum or liquid paraffins, and/or using conventional pharmaceutical auxiliaries, for example tablet disintegrants, solubilizers or preservatives. Thus the product containing the conjugated estrogens can be mixed with pharmaceutical excipients and auxiliaries in known manner and the mixture converted into a suitable dosage form.

In the liquid-liquid extraction described according to the invention, a large number of non-conjugated lipophilic compounds can be removed simply from an aqueous initial phase which may represent either an aqueous solution of a natural mixture of conjugated estrogens from pregnant mares' urine already depleted in phenolic urine contents, an aqueous concentrate of a natural mixture of conjugated estrogens from pregnant mares' urine already depleted in phenolic urine contents, a concentrate of a urine liquid, or a urine concentrate which has optionally been pre-purified by filtration. The non-conjugated lipophilic compounds which are separated include in particular non-conjugated flavonoids, non-conjugated isoflavonoids, non-conjugated norisoprenoids and non-conjugated steroids, such as non-conjugated androstane and non-conjugated pregnane derivatives.

Compared with the conventional liquid-liquid extraction methods, the present invention uses smaller volumes of organic solvents, since a concentrate of the original PMU is always used as aqueous initial phase. If, for example, an aqueous concentrate which has been obtained by the method described in international patent application WO 98/08526 is used for the aqueous initial phase of the liquid-liquid extraction described according to the invention, instead of 5000 liters of PMU only approx. 35 liters of concentrate and correspondingly small quantities of organic solvents are used for the extraction.

If an aqueous solution of a natural mixture of conjugated estrogens from pregnant mares' urine already depleted in phenolic urine contents, or an aqueous concentrate of a natural mixture of conjugated estrogens from pregnant mares' urine already depleted in phenolic urine contents is used as the aqueous initial phase for the liquid-liquid extraction according to the invention, the natural mixture of conjugated equine estrogens obtained as active substance extract, which is depleted in non-conjugated lipophilic constituents and phenolic urine contents, is distinguished by clear optimization of the pharmaceutical specification, as was established according to the invention. In particular an 8 to 20% improvement in the ratio of the conjugated equine estrogens to the dry matter occurs due to the liquid-liquid extraction, without significant losses of conjugated equine estrogens being observed during the extraction process. Thus the aqueous phase obtained in method step (c), which contains the natural mixture of conjugated equine estrogens, compared with the prior art has an advantageous composition and a total hormone content which is increased relative to the dry matter. In this way a quality product is obtained which is distinctly improved e.g. in relation to its composition and its active substance content.

It must be regarded as distinctly surprising that a supposedly simple method of liquid-liquid extraction of an aqueous solution or concentrate of a natural mixture of conjugated estrogens from pregnant mares' urine which is depleted in phenolic urine contents and which contains different and changing quantities of non-conjugated lipophilic constituents contributes in such a way to improving the quality of the resulting active substance extract. In particular, it is very surprising that the proportion of non-conjugated lipophilic compounds, which can fluctuate greatly both in terms of quantity and composition according to the PMU used, can be reduced by the method of the invention so reliably that in method step (c) a mixture of natural conjugated equine estrogens can be obtained as aqueous phase which meets the stringent requirements for pharmaceutical specification, for example the requirements drawn up in accordance with the USP or the European Pharmacopoeia.

Furthermore, it must be regarded as very surprising that when performing the extraction method according to the invention, non-conjugated lipophilic compounds, such as for example defoaming agents, which had previously been added to the PMU as auxiliaries in preceding processing steps, for example in the preparation of the concentrate, also are separated.

It has proved a further advantage of the method according to the invention that the further processing of the extracted concentrate obtained in the form of a natural mixture of conjugated equine estrogens depleted in non-conjugated lipophilic compounds, and its conversion into a galenic form is substantially simplified and facilitated. Surprisingly, the active substance extract obtained with the method according to the invention is distinguished by very good drying behavior and the solids obtained after drying by an extremely good flowability. Thus, for example, the extracted concentrate obtained according to the invention can be applied considerably more easily to excipients than a non-extracted solution. Also the setting of the active substance concentration becomes simplified and reproducible.

The method according to the invention, as already described above in detail, offers a number of advantages and improvements compared with the prior art. Thus the invention makes it possible also to use PMU containing changing quantities of non-conjugated lipophilic constituents, which may, for example, contain an elevated proportion of free flavonoids, free isoflavonoids, free norisoprenoids or free steroid derivatives, in this case in particular of free androstane or pregnane steroids, without the risk of non-compliance with pharmaceutical specifications. With the method according to the invention, a uniform composition of individual extract batches can be ensured, since the non-conjugated lipophilic constituents, the content and composition of which in the PMU may vary according to the type of food ingested by the pregnant mares, are always eliminated, and thus the resulting extracts all have a comparable content of conjugated equine estrogens relative to the dry matter. Furthermore, the separation of the non-conjugated lipophilic constituents achieved with the method according to the invention achieves a higher concentration of the active substances, i.e. the conjugated equine estrogens, in the extract obtained. The method according to the invention additionally also has economic advantages, since the risk of losing valuable active substances if the pharmaceutical specification is not observed, for example in the case of contents of conjugated estrogens relative to dry matter which are not sufficient, is considerably reduced. Furthermore, the application of the method described according to the invention permits substantially more accurate and reproducible setting of the active substance content of the extract obtained. The method according to the invention provides a better quality active substance constituent with an increased hormone content relative to the dry-matter content. This active substance constituent is outstandingly suitable for preparing pharmaceuticals which contain a mixture of natural conjugated equine estrogens as active substance.

The following examples are intended to explain the invention in further detail without limiting its scope.

EXAMPLES

In the following examples, a general operating procedure is given for obtaining active substance extracts from PMU which contain the natural mixture of the conjugated estrogens contained in the PMU and are largely depleted in non-conjugated lipophilic compounds, such as for example non-conjugated flavonoids, non-conjugated isoflavonoids, non-conjugated norisoprenoids, non-conjugated steroids, in particular androstane and pregnane steroids, and comparable non-conjugated compounds. The examples demonstrate how a quality extract with high active substance contents can be obtained according to the invention even from PMU which may have changing or elevated proportions of non-conjugated lipophilic compounds.

Extraction of an Aqueous Concentrate of a Natural Mixture of Conjugated Estrogens from Pregnant Mares' Urine Depleted in Phenolic Urine contents 35.3 kg (Example 1) or 26.7 kg (Example 2) of aqueous concentrate of a natural mixture of conjugated estrogens from pregnant mares' urine already depleted in phenolic urine contents, which was prepared with the aid of the method described in international patent application WO 98/08526 from approx. 5000 liters of PMU, was used as the aqueous initial phase. The dry matter content (DM) and also contents, determined by high performance liquid chromatography (HPLC) and gas chromatography (GC), of conjugated estrogens, for example estrone sulfate salt, and non-conjugated lipophilic compounds, for example formononetin, are shown in the following table of examples for different batches of aqueous concentrate used. This aqueous concentrate was thoroughly mixed in a high-grade steel vat with the aid of a stirrer, while the pH value was adjusted to a value of approximately 5.0 with 1N $H_2SO_4$.

Ethyl acetate (EA—for quantities see following table of examples) was added to the resulting solution in a mixer-settler apparatus in a ratio of 10:8 aqueous phase to organic phase, and the mixture was stirred vigorously for approximately 15 minutes. Thereafter, the mixture was allowed to stand for approximately 90 minutes to separate the phases. Following this, the phases were separated, and ethyl acetate (EA—for quantities see following table of examples) was added to the aqueous phase again in a ratio of 10:2 aqueous phase to organic phase and the mixture was stirred for 15 minutes. After the extraction, the mixture was left to stand for approximately 30 minutes to separate the phases. After the separation of the organic phase, the aqueous phase was transferred to a reaction vessel. Any residues of ethyl acetate still present were distilled off from the aqueous phase under normal pressure.

As a result of the distillation, the dry matter content was adjusted to approximately 9%. Following this, the pH value of the solution was adjusted to approximately 11.0 by addition of 1N NaOH or $Na_2CO_3$. The content of conjugated estrogens of the resulting aqueous extract phase was examined by HPLC and GC analysis. The dry matter content (DM) and also contents, determined by HPLC and GC, of conjugated estrogens, for example estrone sulfate salt, and non-conjugated lipophilic compounds, for example formononetin, are shown in the following table of examples for various batches of aqueous concentrate used. The ratio of the individual hormone constituents to one another, i.e. the relative proportion of estrone sulfate, equilin sulfate and 17-alpha-DH-equilin sulfate in the mixture of conjugated estrogens, may vary in the individual batches owing to the natural fluctuations in the PMU. The desired ratio of the individual hormone constituents relative to each other can be attained by deliberate mixing together of individual batches.

|  | Example 1 | | | Example 2 | | |
| --- | --- | --- | --- | --- | --- | --- |
|  | Content [mg/g] | Quantity [g] | % by weight DM | Content [mg/g] | Quantity [g] | % by weight DM |
| Aqueous initial concentrate |  | 35,300 |  |  | 26,700 |  |
| Dry matter (% by weight) | (9.8) | 3,495 |  | (9.4) | 2,510 |  |
| Conjugated estrogens (total) | 26.2 | 924 | 26.7 | 25.8 | 688 | 27.4 |

-continued

|  | Example 1 | | | Example 2 | | |
| --- | --- | --- | --- | --- | --- | --- |
|  | Content [mg/g] | Quantity [g] | % by weight DM | Content [mg/g] | Quantity [g] | % by weight DM |
| Estrone sulphate | 12.2 | 431 | 12.4 | 16.9 | 452 | 18.0 |
| Equilin sulphate | 9.3 | 328 | 9.5 | 5.8 | 156 | 6.2 |
| 17-alpha-DH-equilin sulfate | 4.7 | 166 | 4.8 | 3.0 | 80 | 3.2 |
| Formononetin | 0.17 | 5.9 | 0.17 | 0.32 | 8.4 | 0.34 |
| 1st EA extraction (ethyl acetate) |  | 25,400 |  |  | 19,400 |  |
| 2nd EA extraction (ethyl acetate) |  | 6,400 |  |  | 4,900 |  |
| Aqueous extract phase obtained |  | 34,000 |  |  | 23,500 |  |
| Dry matter (% by weight) | (8.9) | 3,026 |  | (8.9) | 2,092 |  |
| Conjugated estrogens (total) | 26.3 | 896 | 29.6 | 27.9 | 656 | 31.4 |
| Estrone sulphate | 12.4 | 420 | 13.9 | 18.5 | 434 | 20.8 |
| Equilin sulphate | 9.3 | 317 | 10.5 | 6.3 | 147 | 7.0 |
| 17-alpha-DH-equilin sulfate | 4.6 | 158 | 5.2 | 3.2 | 75 | 3.6 |
| Formononetin | 0 | 0 | 0 | 0 | 0 | 0 |

This extraction method can be performed analogously if instead of the aqueous concentrate of a natural mixture of conjugated estrogens from pregnant mares' urine already depleted in phenolic urine contents, either a concentrate of a urine liquid, a urine concentrate optionally pre-purified by filtration, or an aqueous solution of a natural mixture of conjugated estrogens from pregnant mares' urine already depleted in phenolic urine contents, is used as the aqueous initial phase.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for obtaining a natural mixture of conjugated equine estrogens depleted in non-conjugated lipophilic compounds selected from the group consisting of non-conjugated flavonoids, non-conjugated isoflavonoids and non-conjugated norisoprenoids, said method comprising:
   a) subjecting an aqueous initial phase, selected from the group consisting of
      (i) an aqueous solution of a natural mixture of conjugated estrogens from pregnant mares' urine already depleted in phenolic urine contents comprising phenol, cresol and dihydro-3,4-bis[(3-hydroxyphenyl)methyl]-2(3H)-furanone and obtained by solid-phase or liquid-liquid extraction;
      (ii) an aqueous concentrate of a natural mixture of conjugated estrogens from pregnant mares' urine already depleted in phenolic urine contents comprising phenol, cresol and dihydro-3,4-bis[(3-hydroxyphenyl)methyl]-2(3H)-furanone and obtained by solid-phase or liquid-liquid extraction;
      (iii) a concentrate of pregnant mares' urine liquid, and
      (iv) pregnant mares' urine concentrate, freed from mucilaginous substances and solids by mechanical separation methods, or a concentrated urine retentate obtained by filtration,
   to a liquid-liquid extraction with a sufficient quantity of an organic solvent extracting agent which is at most only slightly miscible with water thereby extracting non-conjugated lipophilic compounds, and subsequently separating a resulting aqueous phase, whereby the organic solvent extracting agent is selected from the group consisting of straight-chained, branched or cyclic $C_4$-$C_{10}$ alcohols, $C_2$-$C_{10}$ esterified acids, $C_3$-$C_{10}$ aldehydes, $C_4$-$C_{10}$ ketones, $C_2$-$C_{10}$ ethers, $C_3$-$C_6$ nitriles and $C_1$-$C_3$ haloalkanes and mixtures of the aforementioned solvents;
   b) optionally repeating method step (a) with the resulting aqueous phase;
   c) recovering an aqueous phase containing the natural mixture of conjugated estrogens depleted in non-conjugated lipophilic compounds selected from the group consisting of non-conjugated flavonoids, non-conjugated isoflavonoids and non-conjugated norisoprenoids;
   d) distilling the recovered aqueous phase to remove residue of the organic solvent extracting agent; and
   e) retaining the distilled aqueous phase from step d) as a starting material for the preparation of medicaments.

2. A method according to claim 1, wherein said extracting agent is immiscible with water.

3. A method according to claim 1, wherein the aqueous initial phase in method step a) comprises (i) an aqueous solution of a natural mixture of conjugated estrogens from pregnant mares' urine already depleted in phenolic urine contents, or (ii) an aqueous concentrate of a natural mixture of conjugated estrogens from pregnant mares' urine already depleted in phenolic urine contents.

4. A method according to claim 1, wherein the extracting agent is selected from the group consisting of $C_1$-$C_4$-alkyl acetates, hexanol, diethyl ether, methylene chloride, methyl tert.-butyl ether and mixtures of two or more of the aforementioned solvents.

5. A method according to claim 4, wherein the extracting agent comprises a $C_1$-$C_4$-alkyl acetate.

6. A method according to claim 5, wherein the extracting agent is ethyl acetate.

7. A method according to claim 1, wherein in method step (a) the aqueous initial phase is adjusted to a pH value in the range from 4 to 12.

8. A method according to claim 7, wherein the pH value in step (a) is in the range from 4.0 to 7.0.

9. A method according to claim 8, wherein the pH value in step (a) is in the range from 4.0 to 6.0.

10. A method according to claim 9, wherein the pH value in step (a) is in the range from 4.7 to 5.3.

11. A method according to claim 1, wherein in method step (a) the volume ratio of the aqueous initial phase to the extracting agent lies in the range from 5:1 to 1:3.

12. A method according to claim 11, wherein the volume ratio of the aqueous initial phase to the extracting agent lies in the range from 2:1 to 1:2.

13. A method according to claim 1, wherein in method step (b) the volume ratio of the aqueous initial phase obtained from step (a) to the extracting agent lies in the range from 20:1 to 1:1.

14. A method according to claim 13, wherein in step (b) the volume ratio of the aqueous initial phase obtained from step (a) to the extracting agent lies in the range from 10:1 to 2:1.

15. A method according to claim 3, wherein the depletion in phenolic urine contents is obtained by solid-phase extraction on a non-ionic semipolar adsorption resin or on a hydrophobized silica gel.

* * * * *